United States Patent
Caso et al.

(10) Patent No.: US 8,952,812 B2
(45) Date of Patent: *Feb. 10, 2015

(54) SYSTEM AND METHOD FOR MEASURING FLUID PRESSURE

(71) Applicant: Tenacore Holdings, Inc., Santa Ana, CA (US)

(72) Inventors: Richard Brand Caso, Mission Viejo, CA (US); Peter John Bonin, Newport Beach, CA (US); James Selevan, Laguna Beach, CA (US)

(73) Assignee: Tenacore Holdings, Inc., Santa Ana, CA (US)

(*) Notice: Subject to any disclaimer, the term of this patent is extended or adjusted under 35 U.S.C. 154(b) by 15 days.

This patent is subject to a terminal disclaimer.

(21) Appl. No.: 13/677,701

(22) Filed: Nov. 15, 2012

(65) Prior Publication Data

US 2013/0069783 A1  Mar. 21, 2013

Related U.S. Application Data

(63) Continuation-in-part of application No. 13/487,955, filed on Jun. 4, 2012, now Pat. No. 8,456,316, which is a continuation of application No. 12/461,064, filed on Jul. 30, 2009, now Pat. No. 8,193,944.

(60) Provisional application No. 61/212,437, filed on Apr. 10, 2009.

(51) Int. Cl.
| | |
|---|---|
| G08B 21/00 | (2006.01) |
| G06F 1/26 | (2006.01) |
| A61M 1/00 | (2006.01) |
| G01L 19/08 | (2006.01) |

(52) U.S. Cl.
CPC .............. *G06F 1/26* (2013.01); *A61M 1/0023* (2013.01); *G01L 19/083* (2013.01); *A61M 2205/3331* (2013.01)
USPC ............. 340/540; 340/686.6; 604/30; 604/67

(58) Field of Classification Search
USPC ............ 340/540, 686.6; 73/708, 753; 604/30, 604/31, 65, 67, 118, 119, 540
See application file for complete search history.

(56) References Cited

U.S. PATENT DOCUMENTS

| | | | | |
|---|---|---|---|---|
| 4,988,336 | A * | 1/1991 | Kohn | 604/67 |
| 6,960,190 | B2 * | 11/2005 | Stinson | 604/119 |
| 7,441,460 | B2 * | 10/2008 | Krupa et al. | 73/753 |
| 8,193,944 | B2 * | 6/2012 | Caso et al. | 340/686.6 |
| 8,456,316 | B2 * | 6/2013 | Caso et al. | 340/686.6 |
| 2001/0035051 | A1 * | 11/2001 | Karlicek | 73/708 |
| 2004/0010223 | A1 * | 1/2004 | Busby et al. | 604/30 |
| 2007/0219532 | A1 * | 9/2007 | Karpowicz et al. | 604/540 |

* cited by examiner

*Primary Examiner* — John A Tweel, Jr.
(74) *Attorney, Agent, or Firm* — Nath, Goldberg & Meyer; Jerald L. Meyer; Katelyn J. Bernier

(57) ABSTRACT

A method of reducing power consumption in a pressure (vacuum) regulator system by waking the regulator upon detection of a person's hand proximity prior to adjustment of a pressure controller, including: defining a sampling time-window to sample a pressure in the pressure regulator system; generating a random number of pressure samples within the defined sampling time-window; acquiring data of the randomly generated number of pressure samples within the defined sampling time-window; adjusting the defined sampling time-window in response to a triggering of a proximity sensor; and wirelessly transmitting the data to an output device.

27 Claims, 8 Drawing Sheets

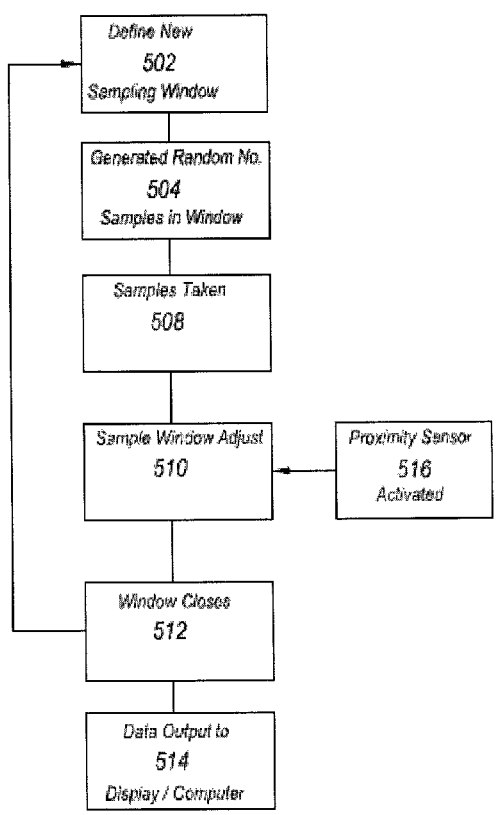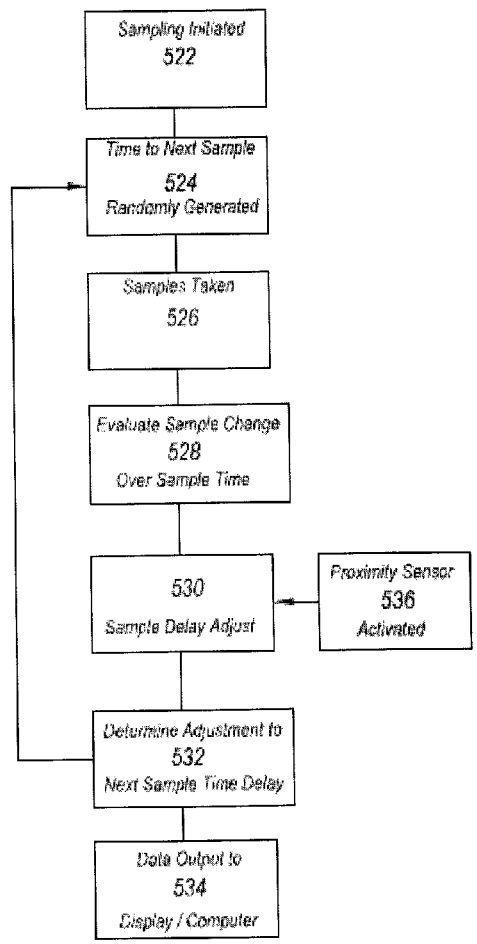
FIG. 5a
FIG. 5b

SYSTEM AND METHOD FOR MEASURING FLUID PRESSURE

CROSS REFERENCE TO RELATED APPLICATIONS

This is a Continuation-in-Part Application of U.S. patent application Ser. No. 13/487,955 filed on Jun. 4, 2012, now U.S. Pat. No. 8,456,316, which is a Continuation Application of U.S. patent application Ser. No. 12/461,064, filed Jul. 30, 2009, now U.S. Pat. No. 8,193,944, which claims priority benefit from U.S. Provisional Patent Application No. 61/212,437, filed Apr. 10, 2009. The contents of each of these are hereby incorporated by reference in their entirety.

BACKGROUND

I. Field

The present disclosure relates to a pressure/vacuum monitoring system. More particularly, the present disclosure relates to an independently powered electronic pressure gauge used to monitor the pressure or vacuum in a gas-fluid system.

II. Background

Pressure regulators can be used to control the level of fluid-gas pressure within an output line attached to a pressure or vacuum source. The pressure regulator generally resides at a location where it can be accessed by an operator for the purposes of reading the level of pressure within the output line and controlling or changing the pressure if desired. The pressure being delivered into the output line can be greater than ambient pressure or it can be below the ambient pressure. In the latter case, where the pressure is below the ambient pressure, the output line generally provides a vacuum and the pressure regulator is a vacuum pressure regulator. Vacuum and above ambient pressure sources are found in various places including machine shops, manufacturing areas, automotive repair areas, hospitals, laboratories, and the like.

Hospital applications for vacuum and pressure sources can be found in the patient room, the operating theater, the catheterization lab, the recovery room, and the like. A vacuum outlet in a room is often found on the wall or in a ceiling drop. Unregulated hospital vacuum sources, which are connected to a centralized vacuum pump system, can range between about 0 and 760 millimeters of mercury (zero to minus 1 atmosphere). The centralized vacuum pumping system generally uses a vacuum pump and a storage tank for the low-pressure fluid, which is generally air. In order for the pressure or vacuum to be of maximum utility, the level of the vacuum or pressure is ideally controlled to within a predetermined range or to a pre-determined level. This control over the vacuum or pressure is accomplished with a pressure regulator.

The traditional vacuum regulator, as used in the hospital environment, calls upon a simple mechanical gauge to display negative pressure applied to the output line. As the practitioner adjusts the vacuum to be applied to the patient, the gauge measures and displays the resultant pressure. The vacuum is used to suction secretions, blood, etc, or to maintain negative pressure in a closed cavity as when inflating a collapsed lung. The mechanical gauge, circular in nature, similar to a clock face, has a dial hand that swings from zero to minus full scale pressure. For example, the gauge might read from 0 to 300-mmHg or 760-mmHg, although other gauge ranges are also available.

Pressure regulating means to display the regulated pressure has traditionally fallen upon mechanical gauges with tried and proven technology and here thereto have been reliant on power from the main. Therefore, there has been a long standing need for a pressure regulator system and method that utilizes a non-mechanical display and also provides power independence for an extended period of time.

SUMMARY

The following presents a simplified summary in order to provide a basic understanding of some aspects of the claimed subject matter. This summary is not an extensive overview, and is not intended to identify key/critical elements or to delineate the scope of the claimed subject matter. Its purpose is to present some concepts in a simplified form as a prelude to the more detailed description that is presented later.

In one aspect of the present disclosure, a method of reducing power consumption in a pressure (vacuum) regulator system is provided by waking the regulator upon detection of a person's hand proximity prior to adjustment of a pressure controller, comprising: defining a sampling time-window to sample a pressure in the pressure regulator system; generating a random number of pressure samples within the defined sampling time-window; acquiring data of the randomly generated number of pressure samples within the defined sampling time-window; adjusting the defined sampling time-window in response to a triggering of a proximity sensor; and wirelessly transmitting the data to an output device.

In another aspect of the present disclosure, a pressure (vacuum) regulator system is provided capable of reducing power consumption by waking a regulator upon detection of a person's hand proximity prior to adjustment of a pressure controller, comprising: means for defining a sampling time-window to sample a pressure in the pressure regulator system; means for generating a random number of pressure samples within the defined sampling time-window; means for acquiring data of the randomly generated number of pressure samples within the defined sampling time-window; means for detecting a proximity; means for adjusting the sampling time-window in response to a triggering of the means for detecting the proximity; and means for wirelessly transmitting the data to an output device.

In yet another aspect of the present disclosure, a reduced power consumption, non-mains pressure (vacuum) regulator system is provided, comprising: a non-mains powered regulator controller capable of sampling pressure values in a sampling time window; an input port and an output port; an adjustment valve coupled to at least one of the input port and output port; a knob attached to the adjustment valve; an output pressure transducer coupled to the output port; and a proximity detector coupled to the controller, wherein the proximity detector upon triggering adjusts a random pressure sampling time-window.

In yet another aspect of the present disclosure, a method is provided of reducing power consumption in a pressure (vacuum) regulator system by waking the regulator upon detection of a person's hand proximity prior to adjustment of the pressure controller, comprising: initiating a sampling of pressure; acquiring a next sampling of pressure after a randomly generated time delay; adjusting the time delay in response to a triggering of a proximity sensor; acquiring another sampling of pressure after adjustment of the adjusted time delay; and wirelessly transmitting the data to an output device.

In yet another aspect of the present disclosure, a pressure (vacuum) regulator system is provided capable of reducing power consumption by waking the regulator upon detection of a person's hand proximity prior to adjustment of the pressure controller, comprising: means for initiating a sampling of pressure; means for acquiring a sampling of pressure after a randomly generated time delay; means for adjusting the time delay in response to triggering of a proximity sensor, wherein the means for acquiring acquires another sampling of pressure after adjustment of the adjusted time delay; and means for wirelessly transmitting the data to an output device.

For purposes of summarizing the disclosed subject matter, certain aspects, advantages and novel features are described herein. It is to be understood that not necessarily all such advantages may be achieved in accordance with any particular embodiment. Thus, for example, those skilled in the art will recognize that the disclosed subject matter may be embodied or carried out in a manner that achieves one advantage or group of advantages as taught herein without necessarily achieving other advantages as may be taught or suggested herein. These and other advantages will be more apparent from the following description taken in conjunction with the accompanying drawings.

BRIEF DESCRIPTION OF THE FIGURES

A general architecture that implements the various features of the disclosed subject matter will now be described with reference to the drawings. The drawings and the associated descriptions are provided to illustrate embodiments of the disclosed subject matter and not to limit the scope of disclosure herein. Throughout the drawings, reference numbers are re-used to indicate correspondence between referenced elements.

FIG. 5a illustrates an exemplary flow chart of another encoding scheme for pressure measurement wherein the measuring interval, within which a random number of samples are taken, is reduced upon detection of the intent to change pressure.

FIG. 5b illustrates an exemplary flow chart of an encoding scheme for pressure measurement wherein the time before the next pressure measurement is reduced upon detection of the intent to change pressure.

DETAILED DESCRIPTION

Figure 1:
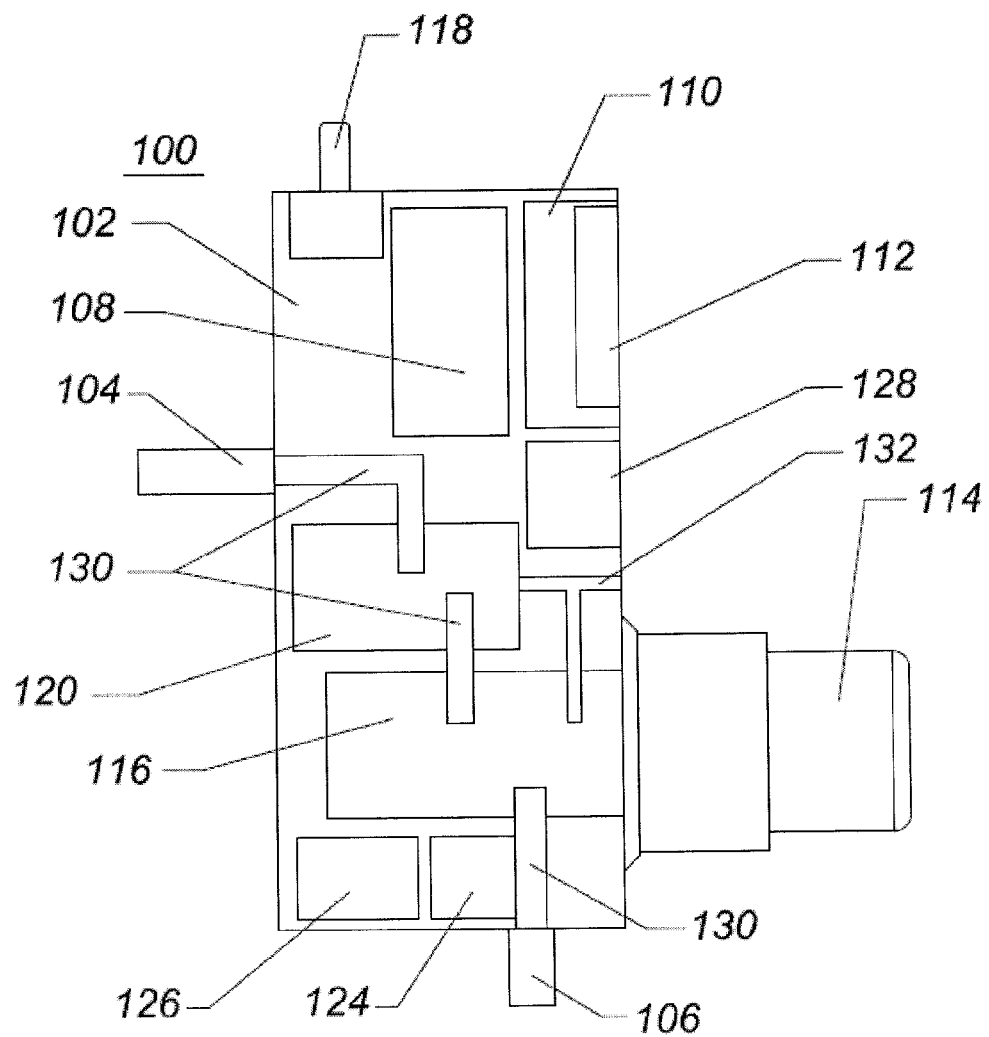
FIG. 1 is a side illustration of an exemplary pressure or vacuum regulator.

The exemplary embodiments disclosed herein may be embodied in other specific forms without departing from its spirit or essential characteristics. The described embodiments are to be considered in all respects only as illustrative and not restrictive. The scope is therefore indicated by the appended claims rather than the foregoing description. All changes that come within the meaning and range of equivalency of the claims are to be embraced within their scope.

As described herein, the use of an electronic measuring and display system provides opportunity to deliver additional information to the practitioner. Low power microcontrollers along with low power pressure sensors allow for a battery-powered electronic gauge, isolated from 60- or 50-cycle main current. Isolation is critical both for patient safety and for user convenience. A battery-powered gauge is mobile, light weight, and un-tethered to an electrical outlet, hence it can be used in remote environments where 60- or 50-cycle main power is not available or not reliable. Furthermore, electronic sensing of pressure allows for feedback control of the regulated pressure. In applications where precise control of pressure is desired, the measured output pressure could feedback, via appropriate amplification, to the regulator control and compensate for drift or fluctuations. In such applications, the use of shape memory alloy wire (Nickel Titanium Alloy), solenoids, servo motor, stepper motor, etc., would provide for mechanical movement and consequent pressure adjustment.

Another important feature of vacuum regulators as they apply to patient care is the ability to intermittently release pressure to ambient. When a negative pressure is applied to a tube situated within a body cavity, fragile tissue can be "sucked" into the orifice of the tube. If maintained for a period of time greater than several seconds to minutes, this trauma to the tissue may result in ischemia, mechanical damage, or bleeding. Thus, intermittent suctioning is desired. This allows for the friable tissue to "float" away from the tube orifice and to minimize damage.

A battery or independently powered pressure regulator, to be of commercial viability, is anticipated to have a 10-year battery life, without need for recharging. Hence, an electronic measuring gauge designed to provide operation for an extended period of time should be designed in such a way as to conserve power most of the time, and yet measure pressure continuously. The device should provide instant feedback to a health care practitioner when an adjustment is made. Various embodiments described herein provide systems and methods for measuring pressure, displaying the results, conserving power, and providing feedback to the health care practitioner when an adjustment of pressure is required.

One aspect of an embodiment(s) is the ability to continuously measure pressure, respond to the practitioner's input, and minimize power consumed. In most applications, pressure will be maintained at a clinically appropriate level for both short and long periods of time (minutes, hours or days). It is anticipated that sampling of pressure can be infrequent during long periods of steady state. The exemplary circuit design described herein allows for the system to enter "sleep" mode during which time the power consumption is minimal (microwatts). However, when adjustment of regulated pressure is required by the clinical situation, the circuit will awaken to monitor pressure continuously, thereby providing instant feedback to the practitioner during pressure adjustment. To avoid any small latency between user input and measured output, it is desirable to detect proximity of the user to the regulator, as one of several possible mechanisms for detecting user input. As a user's hand approaches the regulator to adjust the pressure, the circuitry, acting as a proximity sensor, in this instance, will detect this motion and command the microcontroller and pressure sensor to "wake up" and sample with greater frequency, that is, with smaller time intervals between samples. In a non-limiting example, while in the steady-state clinical setting, where pressure is not being changed, the circuitry might sample once during each 10 second interval (10 seconds just being one of several possible time intervals). When the clinical personnel deems a change in pressure is required, and as their hand approaches the regulator the proximity detector (using any one or more of capacitance, inductance, thermal, ultrasonic, and so forth detection mechanism(s)) will sense this motion and provide an interrupt signal to the microcontroller. At this command, the sampling frequency might be one hundred times per second, providing a mere 10 milliseconds between samples. This frequency of pressure sampling could persist for several seconds to minutes following any perturbation, and then revert back to sleep mode. This provides for instant feedback of pressure change to the practitioner, while providing a very low duty cycle of increased power consumption. Most of the time the circuitry is drawing a few microamps of current, while for a small percentage of time the current requirements would increase to a few milliamps.

Another of a proximity trigger of sampling frequency is that the user could simply "wave" their hand close to the regulator to "wake" it up and increase the sampling frequency (decrease the sampling interval). Hence, if a clinical situation changes or dictates close observation, the user would not have to adjust the regulator to enhance the time-based resolution of the measuring device. Furthermore, as the system "awakens" as a hand approaches, it anticipates a user input, and can be in an increased frequency-of-sampling mode even before any mechanical movement or adjustment of the regulator. Thus, transients associated with pressure sensor power-up are resolved even before the user makes any manual adjustments.

In certain embodiments, the vacuum regulator can sample the pressure in the outlet line at irregular, or random, intervals. An advantage of random interval sampling is that it uses less electrical power than does continuous or regular interval sampling and thus provides less drain on the battery power supply than either of the other two sampling modalities. When the system is not sampling the pressure, it can revert to a dormant or sleep mode to reduce power consumption. The random sampling provides for a low duty cycle operation of the system which optimally saves battery power.

Another feature of random sampling is the ability to cancel out periodic pressure variations. In various embodiments, the sampling interval is performed on a random basis during each given time period. The random sampling prevents the sampling period from coinciding with a mechanical fluctuation of the regulator or vacuum pump. For example, if the pump or regulator has an inherent mechanical oscillation at 10 cycles per second, and the sampling took place at a regular interval of once every 10 seconds, then it is possible that the sample would always occur at a nadir or zenith of pressure. If the pressure is sampled at a regular interval, then cyclic fluctuations of pressure in the main hospital system could synchronize with the sampling frequency and provide an inaccurate measure of true pressure.

Stated differently, sampling could become synchronized with the pressure fluctuations, much as a stroboscope light is synchronized with some linear or angular motion, thereby halting apparent motion. The random nature of the sampling within any given time interval or time-window avoids this potential synchronization, and cancels out either periodic or non-periodic fluctuations in the input pressure/vacuum line. The sampling window, or interval, can range from about 0.1 seconds to about 100 seconds with a range of about 5 seconds to 20 seconds. The actual frequency of sampling is random within an infinite expanding range. The range would expand based upon user inactivity. For example: if the random sampling interval is every 2 seconds during the first hour after perturbation, the sampling interval would increase over time (minute-to-minute; hour-to-hour; etc.) provided the user has not incited the proximity switch. In this way the controlling circuit has "learned" from the user's activity, decreasing sampling frequency (increasing sampling interval) in accordance with the clinical need. This represents a unique power saving approach.

In certain embodiments, the system can operate using a power supply that is provided by the mains in the room. In other embodiments, the power supply can be a battery contained within the pressure regulator or affixed thereto. In some embodiments the battery can be non-rechargeable, while in other embodiments, the battery can be rechargeable. The battery charger can be internally or externally mounted to the regulator or it can be an entirely separate device that is affixed by a connecting wire and plug, for example, or it can be in close proximity to allow for inductive (non-contact) charging. Such inductive charging avoids direct electrical connection to 60/50-cycle high-voltage conductors. In the hospital or clinic setting, such exposure to 60/50-cycle current is potentially dangerous and to be avoided.

It should be appreciated that while the term "battery" is used herein to describe an independent source of power for the exemplary regulating system, a non-battery device or mechanism, such as a fuel cell, capacitor, energy storage device and so forth may be used without departing from the spirit and scope of this disclosure.

In certain embodiments, the system can be configured to provide an audio alarm, a visual alarm, or both, should the pressure in the output line, the input line, or both, vary beyond a confidence band around the set point or points. In other embodiments, the control unit can provide signal alarms to remote stations using radio frequency, microwave, infrared, local area network, or other communications means. Alarms can be used by attending personnel to generate an alert when an out of compliance condition exists within the system, said condition requiring attention and potential adjustment. In a vacuum regulator system, for example, a vacuum line to a patient can become kinked, blocked, filled with debris, or otherwise rendered inoperable. Such an event could cause a change in vacuum pressure or flow such that an alarm would be tripped once the sensors measured the event and compared it to the desired set-point range.

In some embodiments, the rate of pressure sampling or the total number of samples per unit time can be increased upon some perturbation in the system that might require attention on the part of the controller to change the pressure or vacuum applied to the patient. Such perturbations in the system that could result in increasing the sampling rate, or stated alternatively, reducing the sampling interval, include rapid decrease in flow such that might be seen with an obstructed tube in a body orifice. For example, if the sampling frequency is once every 10 seconds, then should an obstruction of the tube occur, the microcontroller would "wake up" and increase the sampling frequency, providing almost instant change in the displayed pressure or alarm.

In various embodiments, however, a proximity switch can comprise a capacitance sensor, inductance sensor, ultrasonic sensor, etc., that senses the user's hand in close proximity to the regulator. The sensor and associated control circuitry triggers the microcontroller to increase the sampling interval. Thus, a simple "wave of the hand" towards the wall-mounted regulator would invoke a change in sampling frequency.

FIG. 1 illustrates a side view of a pressure regulator 100 with internal components shown in block form. The pressure regulator 100 comprises a case 102, an input port 104, an output port 106, a controller 108, a selector switch 118, a control valve 120, an adjustment valve 116 further comprising a knob 114, an output pressure transducer 124, a transducer bridge amplifier 126, a display controller 110, an audio output device 128, and a visual display 112.

Referring to FIG. 1, the case 102 houses all the other components, or the other components are affixed thereto. The input port 104 is affixed to the case 102 and further comprises a hollow interior lumen through which fluid can flow into or out of (vacuum) the regulator 100. The output port 106 is affixed to the case 102 and further comprises a hollow lumen through which fluid can flow into or out of the regulator 100. The input port 104 and the output port 106 are operably connected by tubing, channels, or hollow pipe 130 with intervention by various valves. Air channel(s) 132 is connected to the control valve 120 and (optionally) adjustment valve 116. The control valve 120 resides between the input port 104 and the output port 106 and restricts or opens the channel for flow therebetween in response to electrical or fluidic signals received from the controller 108. The controller 108 can comprise a computer, memory, input-output devices, embedded software, and other components commonly found in electronic control devices. The controller 108 can be operably connected to the control valve 120 via a bus, wiring, electrical interconnects, or the like (not shown). The controller 108 can be further connected to the output or visual output controller 110 with electrical wiring, a bus, interconnects, or the like (not shown). The controller software can be isolated, or it can be rendered upgradeable using infrared, short-distance radio frequency, other wireless means, or simple wiring means such as USB, and so forth.

The input of the audio output device 128 is operably connected by electrical wiring to an output of the controller 108. The audio output device 128 is affixed to the case 102 and can be a buzzer, a loudspeaker, or other sound generation device along with appropriate amplification, frequency synthesis, and volume control systems as according to design preference. The display controller 110 is electrically connected at its input to an output line of the controller 108. The output of the display controller 110 is operably connected with an electronic bus to the input port of the visual output device 112. The display controller 110 and the visual output device 112 can be affixed to the case 102 or other intermediate structures.

The visual output device 112 can comprise a cathode ray tube (CRT), liquid crystal display (LCD), a light emitting diode (LED) array, single LEDs, and so forth. The visual output device 112 can be configured to output data such as, but not limited to, set pressure, output line pressure, time, battery level, alarm mode, warning mode, etc. The audio output device 128 can generate single tones, modulated tones, musical notes or strings of musical notes making up a tune, informational tones such as in the case of spoken language, and the like.

In some embodiments, the audio alarm could be configured for different conditions—such as when the vacuum pressure exceeds 165 mm/Hg, as one possible example of a threshold alarm condition. This value could be hard coded into the microcontroller and would be appropriate for pediatric clinics, for example. Of course, other alarm conditions could be devised, suited for standard or surgical or any other clinic or situation desired. Each of these conditions may be hard coded or modifiable by the clinician by selecting a switch or other mechanism—thus adjusting the threshold(s) for alarming.

It should be understood that with advances in electronics, the display controller 110 and the controller 108 may be facilitated by a single device/chip/processor, as well as with transducer bridge amplifier 126. Therefore, it is expressly understood that the exemplary embodiments are not constrained to have separate controllers 110 and 108, etc.

Figure 2:
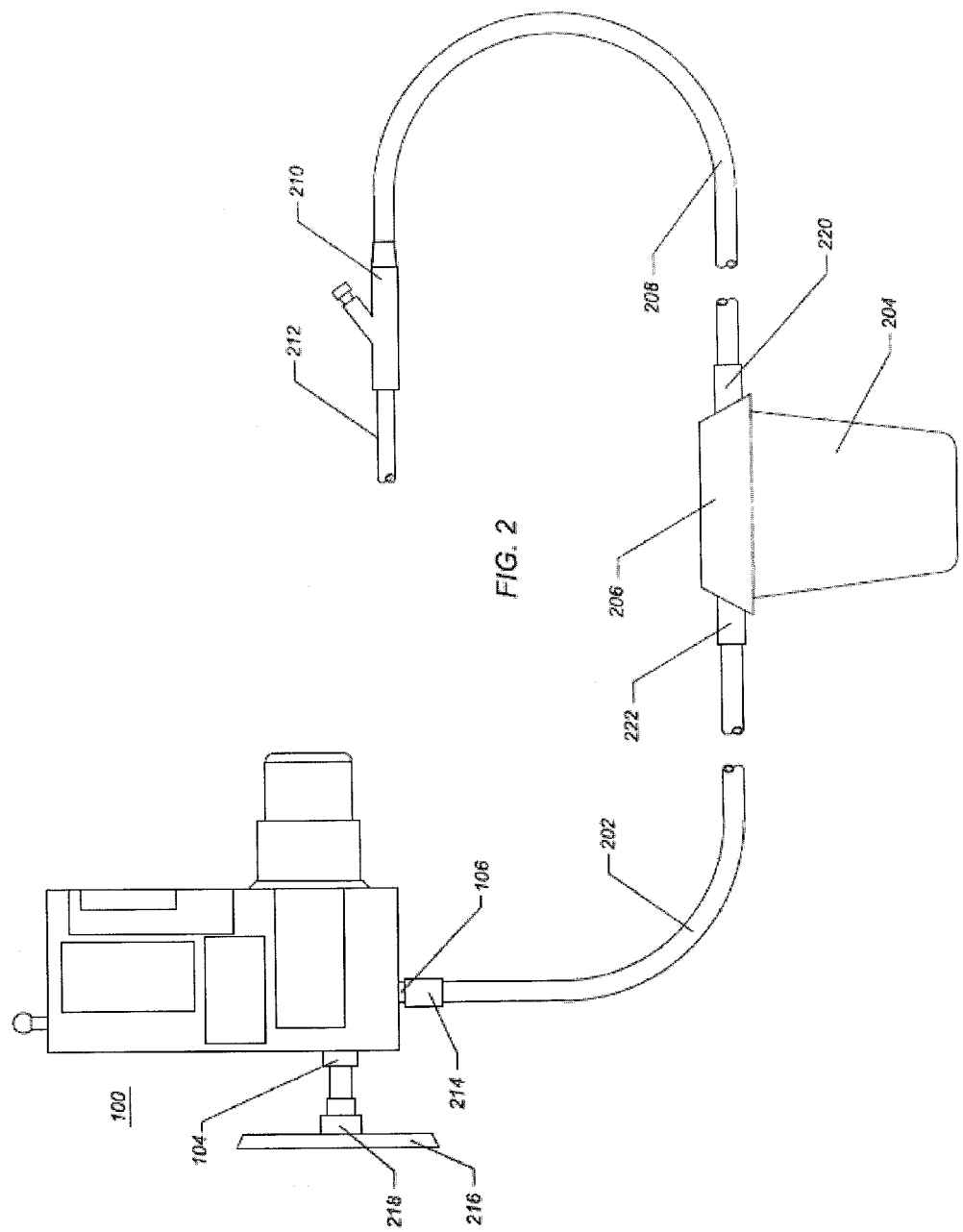
FIG. 2 is an illustration of an exemplary vacuum regulator as used in an operating room to pull suction on a chest drainage tube.

FIG. 2 illustrates an exemplary pressure regulator 100 connected to a cardiotomy reservoir 204, pleural evacuation chamber, or the like via a length of vacuum output tubing 202. The pressure regulator 100 is configured as a vacuum regulator in this embodiment and is affixed to, as well as being operably connected, at its input port 104, to a wall vacuum outlet 218, which is affixed to a wall plate 216. The reservoir 204 further comprises a fluid input plenum 206 further comprising a vacuum output port 220 and a vacuum source port 222.

The vacuum source port 222 is operably connected to the vacuum output tubing 202, which is operably connected to the vacuum output line 106 of the regulator 100 via optional coupler 214. The vacuum output port 220 is operably connected to a vacuum line 208, which is affixed to the proximal end of a suction catheter or drainage tube 212 at its hub 210.

The pressure regulator 100 is configured to maintain suction, or vacuum, that is sufficient to remove fluid and debris from a patient (not shown) through the drainage tube 212 but not so great as to cause tissue damage. Thus, careful control of the pressure regulator 100 output is necessary and desirable. For instance, the drainage tube 212 can be placed such that its distal end resides within the patient's pleural space to serve as a chest drainage tube for a pneumothorax. Loss of suction could cause the lung to re-collapse so maintenance of a correct vacuum is imperative, as is the need to monitor for the presence of blockage with the chest tube such that if the vacuum becomes compromised within the patient, a caregiver will be notified so that remedial action can be initiated to remove the blockage. The reservoir 204 is configured with the vacuum input port 222 high, as is the vacuum output port 220. Thus, liquid that drains from the patient will collect in the container of the reservoir 204 and not be introduced into the regulator 100 by way of the vacuum line 202.

Figure 3:
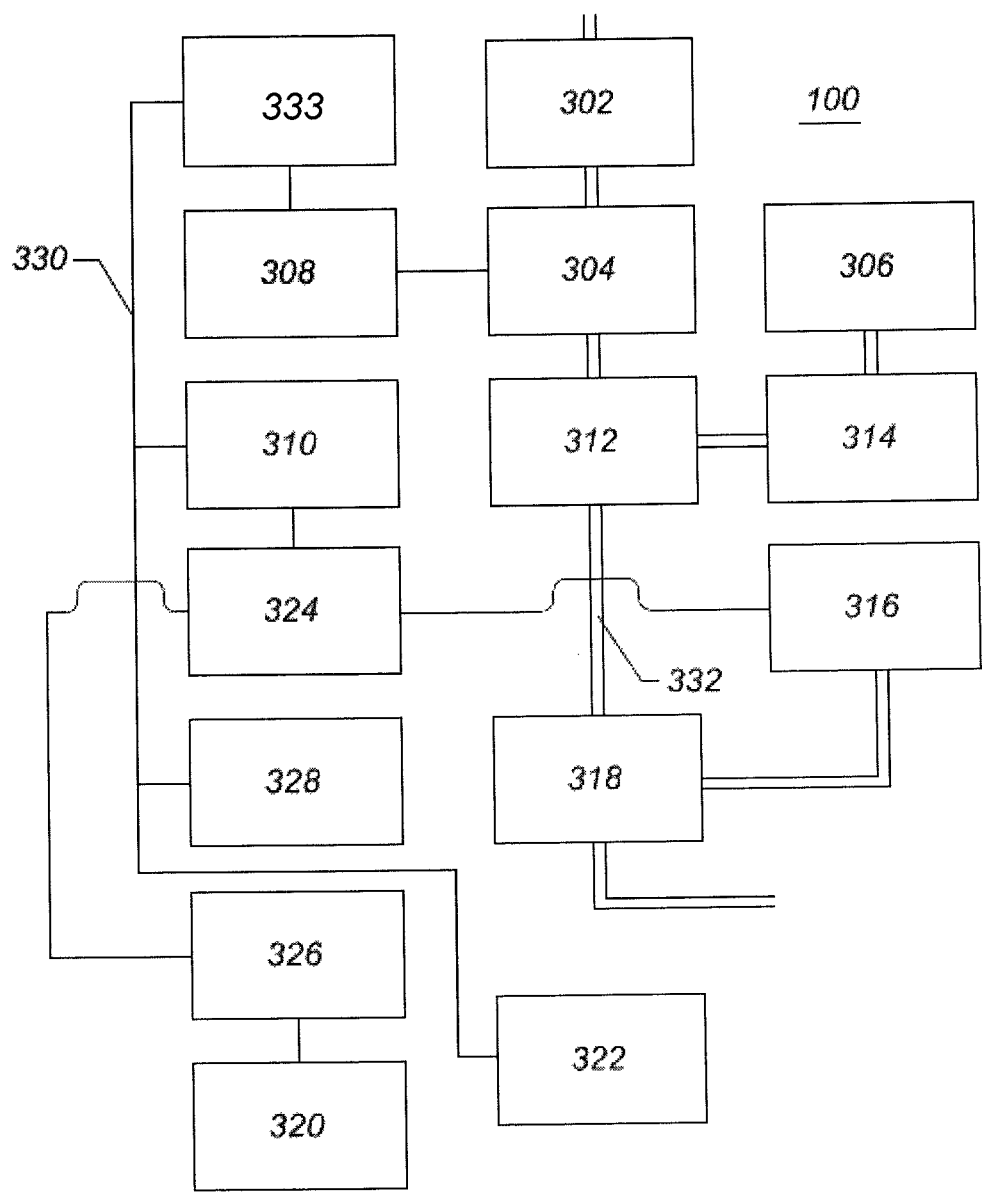
FIG. 3 illustrates a block diagram of the components of an exemplary pressure regulator.

FIG. 3 illustrates a block diagram of an exemplary pressure regulator 100. The pressure regulator 100 comprises a fluid input port 302, an adjustment valve 304, a pressure accumulator 312, a pressure output port 318, an output line pressure sensor 316, a bridge amplifier 324, a display processor 326, a visual display device 320, a battery 328, a controller 310, an adjustment device 308, an intent to modify sensor 333, an ambient air vent 306, a control valve 314, and an audio output system 322. The components are operably, electrically connected by a wiring bus 330, illustrated with a single line, and they are operably, fluidically connected by a fluid line 332, illustrated with a double line.

Referring to the diagram of FIG. 3, all electrical components may be operably electrically connected, for example, using electrical wiring, a wiring bus, a wireless interface, or a combination thereof. The electrical connections can be digital, analog, or a combination thereof. The fluid input port 302 is operably connected to an external pressure source (not shown). The fluid input port 302 is connected to the control valve 304, either directly or indirectly, by a length of tubing, pipe, a manifold, or other leak-free fluid conducting structure. The output line 318 is operably connected to the pressure accumulator 312 by a portion of the fluid conduit 332. The pressure sensor 316, which can be a typical pressure transducer that uses changes in resistance, voltage, or the like and is fluidically coupled to the output line 318, the accumulator 312, or the connecting fluid conduit 332. The pressure sensor 316 can be electrically connected to the bridge amplifier 324, or similar device, which is electrically connected to the controller 310 and the display processor 326 by the electrical bus 330. In an alternative embodiment, the pressure sensor is self-contained, with appropriate sensor, amplifier, and analog to digital converter, all packaged in a device that can be attached to a printed circuit board. This attachment may use wave-soldering techniques, hand soldered, inserted, etc. The display processor 326 is electrically connected to the visual display 320 by the electrical bus 330. The audio output system 322 can be electrically connected to the controller 310 or the bridge amplifier by the electrical bus 330.

Figure 4A:
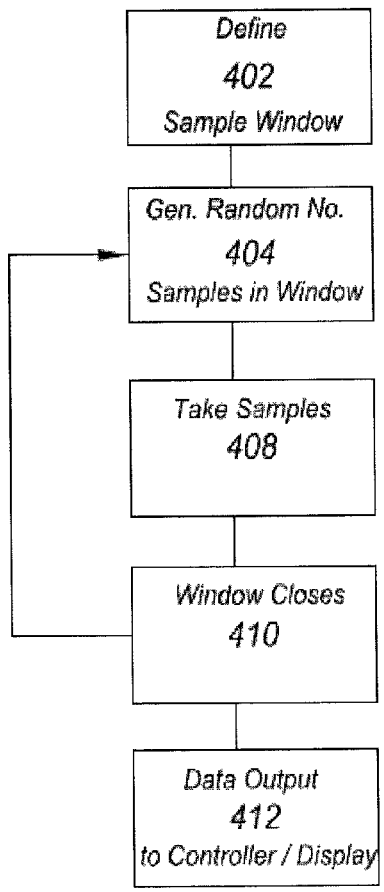
FIG. 4a illustrates a flow chart of an exemplary encoding scheme for pressure measurement wherein the number of samples taken within a sampling interval is randomly generated.

FIG. 4a illustrates a flow chart of an exemplary encoding scheme for pressure measurement wherein the number of samples taken within a sampling interval is randomly generated. The encoding scheme illustrated in FIG. 4a can be hard wired or it can be generated using software, either embedded or provided from an external input. The encoding scheme comprises defining a sampling time-window 402, generating a random number of samples 404 within the sampling window 402, taking the samples 408 in accordance with the sampling rate generated in step 404, closing 410 the time-window, and then simultaneously displaying 412 the output on a visual output device (or sending 412 the data to a controller), and returning from step 410 to generate another random number of samples 404 within the sampling time-window 402. With no further intervention, this program continues to run in a random fashion in such a way as to minimize the amount of electrical energy required in the sampling process. When not taking a sample, the microcontroller brings the entire display and control circuitry into "sleep" mode, thereby minimizing power consumption. Upon detecting an "intent" to change pressure, as when a user's hand approaches the device, the microcontroller "wakes up" and begins sampling at a much more frequent rate.

Figure 4B:
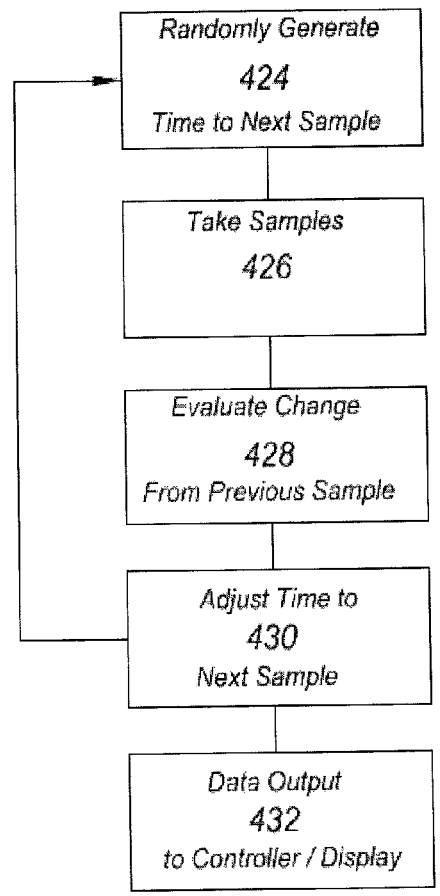
FIG. 4b illustrates an exemplary flow chart of an encoding scheme wherein the time to acquisition of the next sample is randomly generated, with an option to modify the time to next sample as a function of the magnitude of the pressure change since the last measurement.

FIG. 4b illustrates a flow chart of an exemplary encoding scheme wherein the time to acquisition of the next sample is randomly generated, with an option to modify the time to next sample as a function of the magnitude of the pressure change since the last measurement. The sampling methodology, as encoded within the instruction set of the system, comprises randomly generating a new time to next sample 424, taking one or more samples 426 once the time to next sample 424 has elapsed, evaluating 428 the change in pressure, and adjusting the time to the next sample 430. These data are then sent to the display or controller 432. The time to the next sample 424, is modified by the time adjustment 430.

FIG. 5a illustrates a flow chart of another exemplary encoding scheme for pressure data measurement wherein the measuring interval, within which a random number of data samples are taken, is decreased upon proximity detection. That is, instead of taking random samples, the samples are taken at more frequent intervals. In some embodiments, the randomness of sampling may be continued, however, with the sampling frequency increased. The encoding scheme, or method, can be embedded in firmware, software, memory, externally input, hardwired, or the like. The method comprises defining a new sampling time-window 502, generating a random number of samples 504 within the sampling time-window 502, taking 508 the randomly generated number of samples 504 within the sample time-window 502, adjusting 510 the sample time-window in response to activation of a proximity sensor 516, closing 512 the sampling time-window, transmitting the data to an output device or controller 514, while also looping back to define a new sampling time-window 502 and beginning the scheme again.

Activation of the proximity sensor 516 can comprise moving a hand close to a sensor, for example, embedded within the wall-mounted regulator such that the presence of the human hand or object can be detected by the proximity sensor. The proximity sensor can be an impedance sensor, capacitance sensor, motion sensor, inductance sensor, ultrasonic detector, and so forth. The sample time-window adjustment 510 generally comprises shortening the length of the sampling time-window so that additional samples are taken within a given period of time. The sample time-window adjustment 510 can further comprise evaluation of changes, more specifically a lack thereof, in the pressure measurements such that when pressure remains constant for a period of time, the sampling time-window can be increased, or opened up to provide fewer samples per unit time. The sample time-window adjustment 510 can also comprise evaluation of changes in pressure such that significant changes in pressure over a given period of time can result in reducing the sample time-window to a smaller value such that more samples are taken in a given time period. Thus, should an obstruction in the line either within a body cavity or external to the patient's body occur, the resultant change in pressure would trigger an increased frequency of sampling (that is, a decrease in sampling interval) and if reproduced over several samples could trigger an audible or visual warning signal, or in the event of a threshold value being exceeded.

FIG. 5b illustrates a flow chart of an encoding scheme for pressure measurement wherein the time before the next pressure measurement is reduced upon detection of intent to change pressure. The method comprises initiating pressure or data sampling 522, generating a random time until acquisition of the next sample 524, taking the sample or samples 526, evaluating any change in the pressure 528, adjusting a sample delay 530 in response to activation of a proximity sensor 536, determining an adjustment to the next sample time delay 532, and then looping back to define a new time to next sample 524 while at the same time sending the data for display 534.

The encoding scheme of FIG. 5b provides a logic analysis of activation of a proximity sensor 536 such that an adjustment can be made to the time to acquisition of the next data packet. Typically, activation of the proximity sensor will decrease the time to the next sample due to anticipated changes in the system pressure occurring. Following a period of no or minimal change, the time to next sample can be adjusted to a larger number. For example, if the random number generator determined the time to next sample to be 1 minute and there was no proximity sensor activation, the delay would remain 1 minute. However, if the proximity sensor was activated, it might reduce this time period by 99% for the next sample such that the actual delay would reduce to milliseconds. The system might sample every 50 milliseconds, as one example, for a period of time until the pressure stabilized, at which point, the randomly generated time delay would return to the "sleep" mode interval of many seconds.

Figure 6:
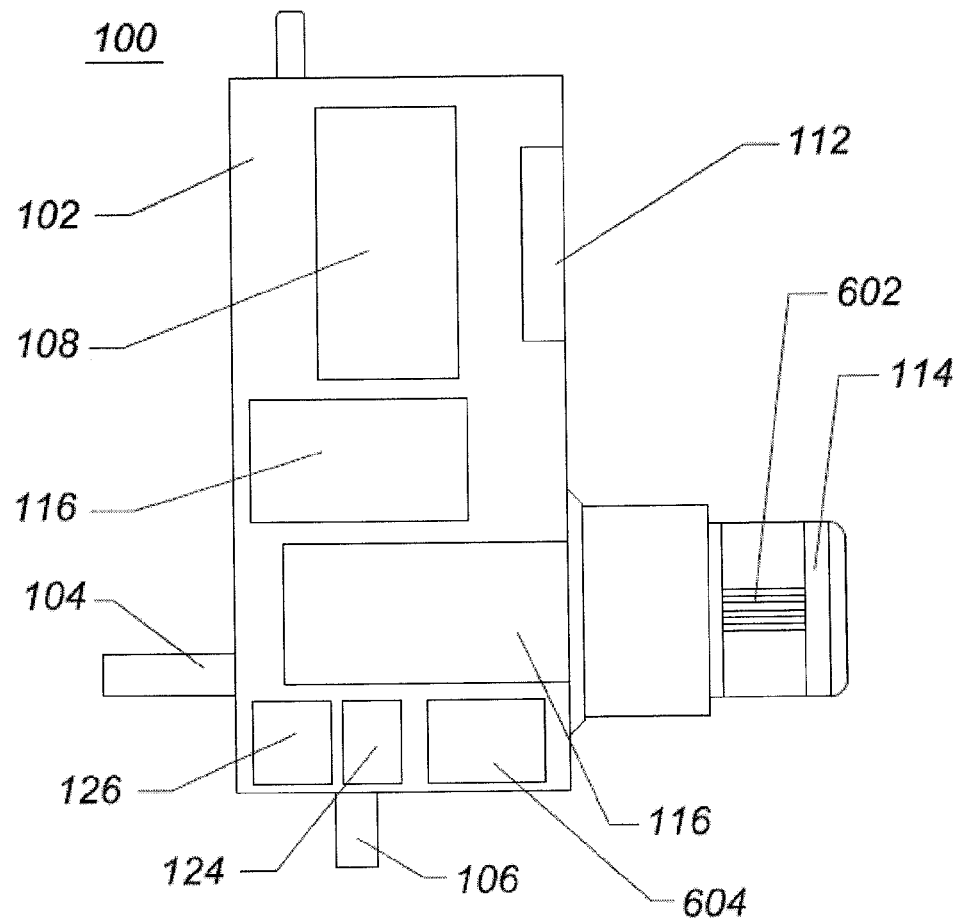
FIG. 6 illustrates a side block view of an exemplary detection system for intent to change pressure integrated into a pressure or vacuum regulator.

FIG. 6 illustrates a side block view of a detection system for intent to change pressure integrated into a pressure or vacuum regulator 100. The vacuum regulator 100 comprises the pressure input port 104, the pressure output port 106, the adjustment knob 114, the proximity sensor 602 embedded within the regulator case 102, the proximity sensor support electronics 604, the control valve 116, the controller 108, the case 102, the visual display 112, the pressure sensor 124, the bridge amplifier 126, and the adjustment valve 116.

Referring to FIG. 6, the proximity sensor 602 may be affixed to the inside of the case 102. The location of the proximity sensor element will be determined by the physical dimensions of the case 102, and may be located in the knob 114, along the face of the case, along the side of the case, etc. The location of the proximity sensor element may be based on sensitivity requirements, the physical layout of the internal components of the regulator, and the material used for the case of the regulator, and so forth. The nature of the construction material of the case 102 may be determined by cost, toxicity, durability, etc., and may be plastic, metal, or other material. The proximity sensor 602 feeds input to the proximity sensor support electronics 604, which, in turn feeds electronic signals to the controller 108. The controller 108 alters the sampling intervals or sampling delays for the pressure sensor 124 and its bridge amplifier 126, and the like. The output of the bridge amplifier 126 can be input to the controller 108 and ultimately end up in the visual display 112. The proximity sensor 602 can comprise an impedance sensor, a capacitance sensor, a motion sensor, and the like. The pressure sensor 124 can be operably set to sample the pressure in the output line 106, the input line 104, or both.

In certain embodiments, the vacuum regulator comprises visual output devices such as, but not limited to, LCD, LED, or other displays. In some embodiments the vacuum pressure regulator comprises audio output devices such as, but not limited to, loudspeakers, buzzers, bells, vibrators, or the like. The output devices are controlled by electronic circuitry that is electrically, operably coupled to a microprocessor or other controller that monitors pressures and changes in pressure per unit of time. Output of a digital-electronic measuring device can be used, for example, to control a mechanical regulator in a feedback-control system. A clinician can set a desired pressure, and a feedback system can adjust the vacuum or pressure applied to a patient to maintain a predetermined setting. This allows for automatic, semi-automatic, or manual compensation in response to events that alter an applied pressure or vacuum. Exemplary events include, but are not limited to, partial obstruction of suction or pressure tubing, a change in viscosity of a fluid added or removed from a system or body cavity, a change in pressure in a "mains" hospital system vacuum pump, a system leak, a pump malfunction, and sealing of a body cavity caused by tissue scarring, blood clotting, or some other obstruction.

Figure 7A:
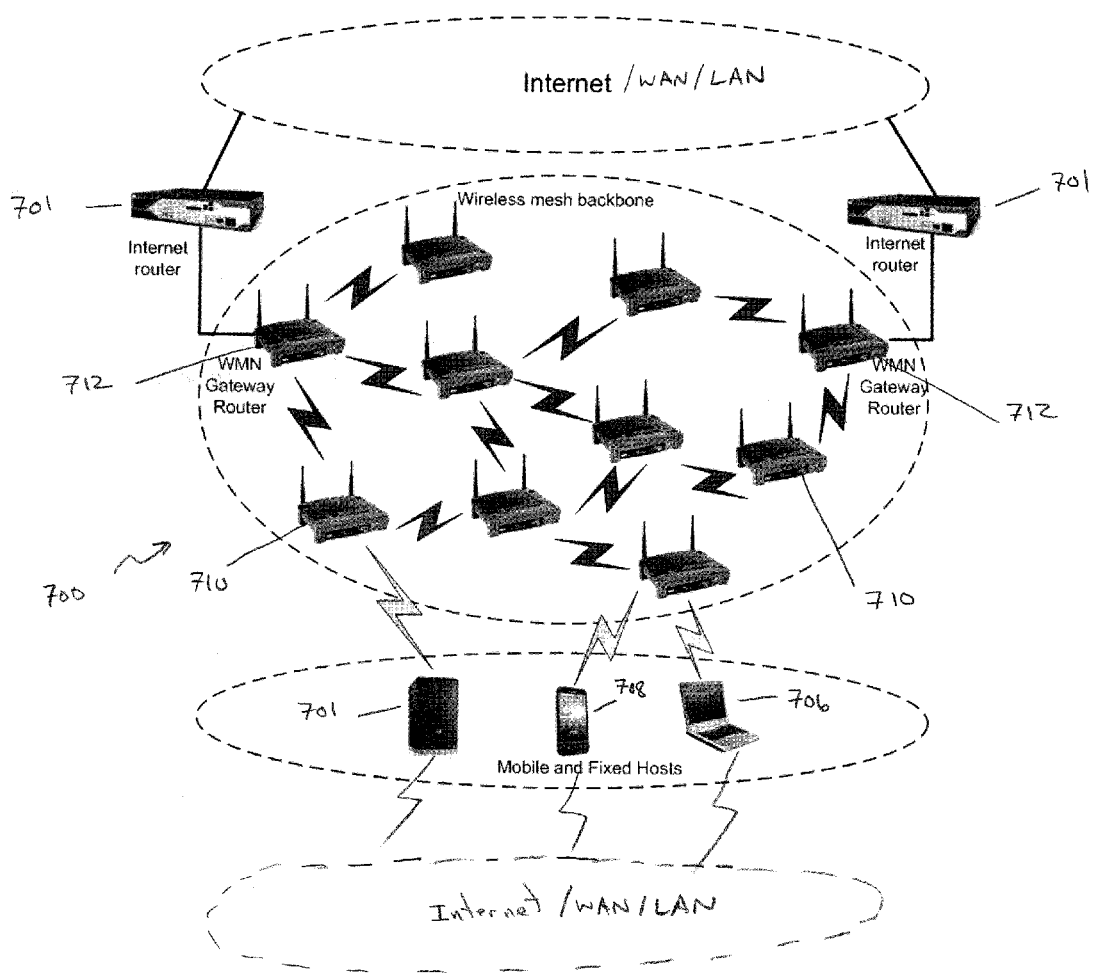
FIG. 7a illustrates a first exemplary mesh network for use with pressure/vacuum monitoring systems.
Figure 7B:
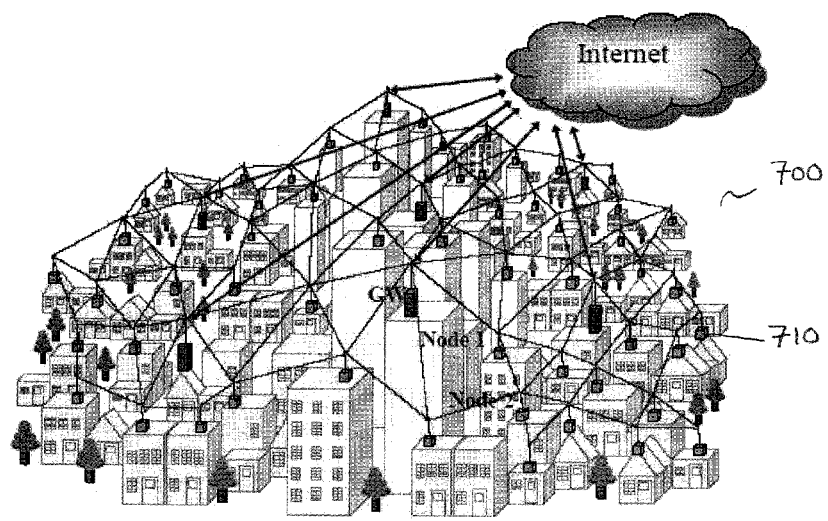
FIG. 7b illustrates a second exemplary mesh network for use with pressure/vacuum monitoring systems.

FIGS. 7a and 7b illustrate exemplary embodiments of the claimed subject matter where data and/or control signals (generically referred to as information) are transmitted and/or received via a mesh network 700. Data may include, for example, battery status, pressure measurement in real time, maximum pressure, minimum pressure, pressure profile (X-Y plot of pressure over time), and evidence of an alarm event such as mains pump failure, tube obstruction, or system leak. Control signals include but are not limited to any signal used to control at least one item in a network. This information is transmitted via at least one of a wired connection 702, a wireless connection 704, or a combination of the two. The exemplary network 700 is shown connected to the Internet, but need not be. The network 700 could connect instead of or in addition to a wide area network (WAN) and/or a local area network (LAN). Other connections may be used without departing from the scope of this subject matter. Exemplary transmission methods include but are not limited to transmission via a radio frequency signal, a light signal, a signal transmitted by wire, or any combination of these. Information can be transmitted anywhere in the world using, for example, a central switch, router, or hub (generically referred to as a server) 701; a computer 706; a smart phone, a tablet, a netbook, or general wireless device 708; or a virtual desktop (not shown). A physician may be notified of an obstructed thoracic suction tube via e-mail generated by a suction device in a hospital in a different country. Information can also be transmitted via a wired connection, via land line, or other information transmission means known to those of skill in the art.

In the exemplary mesh network of FIG. 7a, connections are spread among one or more nodes 710, with each node 710 connecting with at least one other. A node 710 can be anything with a network transceiver. Non-limiting examples include a USB hard disk, a telephone, even an airliner. Nodes 710 communicate with each other to route messages amongst themselves without the need for a traditional, hierarchical routing model. This allows nodes 710 to join, move among, and drop out of the network 700 without having to make administrative changes. Connections can be wired, wireless, or any combination of the two. Only one node 710 needs to be physically wired to a network connection, although multiple nodes can be physically wired if desired. A physically wired node is called a wired node 712. A wired node 712 then shares its connection with other nodes. Connections to other nodes 710 can be wireless, but need not be. In certain exemplary embodiments, mesh networks are "self configuring", where the network automatically incorporates a new node 710 into an existing structure without needing adjustments by a network administrator. Some mesh networks are "self healing", where the network automatically finds the fastest and most reliable paths to send data, even if some nodes 710 are blocked or lose their signal.

As shown in FIG. 7b, mesh networks can connect entire cities or even countries. The more nodes 710, the farther the connection spreads. Thus, a network could be within a single room, a building, a city, or even across continents. Mesh networks are often used when nodes 710 are located at scattered points that do not lie near a common line. These networks need not have designated routers. Instead, nodes serve as routers for one another, with data passing from node to node in a process called hopping. A connection can be rerouted around broken or blocked paths, with a signal hopping from node to node until it reaches its destination. If one node can no longer operate or is out of range of another node, the rest can still communicate with each other, directly or through one or more intermediate nodes.

Figure 8:
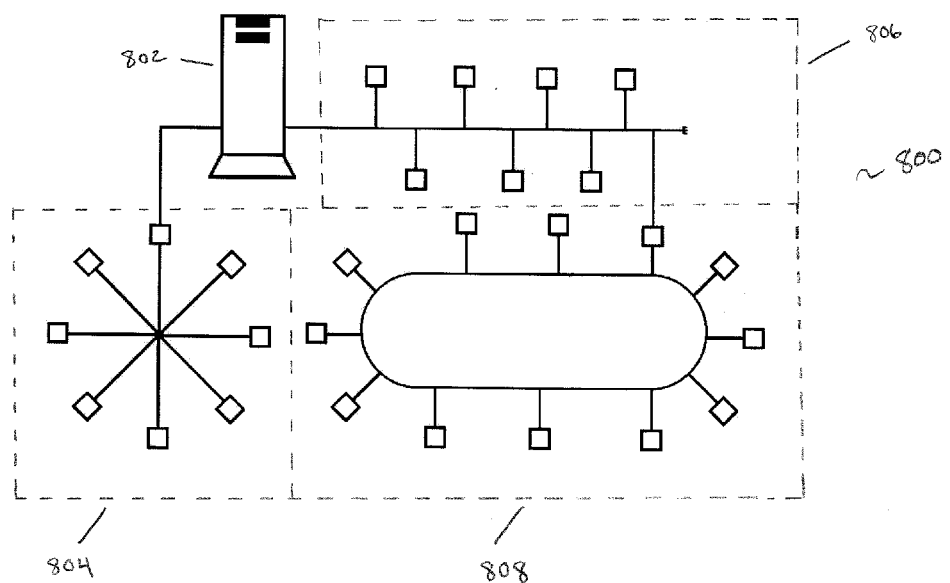
FIG. 8 illustrates an exemplary hybrid network for use with pressure/vacuum monitoring systems.

One of skill in the art would understand that the network is not limited to a mesh configuration. FIG. 8, for example, illustrates an example of a hybrid network 800. Hybrid networks 800 use a combination of any two or more topologies such that the resulting network does not exhibit one of the standard topologies (e.g., bus, star, ring, etc.). The non-limiting exemplary hybrid network 800 of FIG. 8 includes a central switch, router, or hub (generically referred to as a server) 802 with links interconnected (logically and/or physically) in configurations resembling a star configuration 804, a bus configuration 806, and a ring configuration 808. Other configurations can also be used without departing from the scope of the subject matter. For example, a tree network configuration (not shown) or other configurations known to those skilled in the art could also be used.

Aspects of the claimed subject matter may be implemented as a method, apparatus, or article of manufacture using standard programming and/or engineering techniques to produce software, firmware, hardware, or any combination thereof to control a computer or computing components to implement various aspects of the claimed subject matter. The term "article of manufacture" as used herein is intended to encompass a computer program accessible from any computer-readable device, carrier, or media (transient or non-transient). For example, computer readable media can include but are not limited to magnetic storage devices (e.g., hard disk, floppy disk, magnetic strips), optical disks (e.g., compact disk (CD), digital versatile disk (DVD)), smart cards, and flash memory devices (e.g., card, stick, key drive). Additionally it should be appreciated that a carrier wave can be employed to carry computer-readable electronic data such as those used in transmitting and receiving voice mail or in accessing a network such as a cellular network. Of course, those skilled in the art will recognize many modifications may be made to this configuration without departing from the scope or spirit of what is described herein.

What has been described above includes examples of one or more embodiments. It is, of course, not possible to describe every conceivable combination of components or methodologies for purposes of describing the aforementioned embodiments, but one of ordinary skill in the art may recognize that many further combinations and permutations of various embodiments are possible. Accordingly, the described embodiments are intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

The above presents a description of the devices and methods contemplated for carrying out the present neurointervention and methods of providing said neurointervention, and of the manner and process of making and using the devices, in such full, clear, concise, and exact terms as to enable any person skilled in the art to which it pertains to make and use these neurointerventional devices and methods. These devices and methods are, however, susceptible to modifications and alternate constructions from that discussed above that are fully equivalent. Therefore, the various examples and embodiments disclosed herein may be applicable in non-medical arenas. Consequently, these devices and methods are not limited to the particular embodiments disclosed. On the contrary, these devices and methods cover all modifications and alternate constructions coming within the spirit and scope of the devices and methods are as generally expressed by the following claims, which particularly point out and distinctly claim the subject matter of these devices and methods.

What is claimed is:

1. A method of reducing power consumption in a pressure (vacuum) regulator system by waking the regulator upon detection of a person's hand proximity prior to adjustment of a pressure controller, comprising:
    defining a sampling time-window to sample a pressure in the pressure regulator system;
    generating a random number of pressure samples within the defined sampling time-window;
    acquiring data of the randomly generated number of pressure samples within the defined sampling time-window;
    adjusting the defined sampling time-window in response to a triggering of a proximity sensor; and
    wirelessly transmitting the data to an output device.

2. The method of claim 1, further comprising closing the adjusted sampling time-window.

3. The method of claim 1, further comprising sending at least one of continuous and intermittent pressure information via email.

4. The method of claim 1, further comprising reducing the size of the adjusted sampling time-window.

5. The method of claim 1, further comprising returning the adjusted sampling time-window to its initial defined value following a predetermined period of negligible change in the acquired data.

6. The method of claim 1, further comprising the step of transmitting the data via a mesh network.

7. The method of claim 1, further comprising the step of selecting the output device from the group consisting of a computer, a smart phone, a tablet, and a netbook.

8. The method of claim 1, wherein the proximity sensor is a motion sensor.

9. The method of claim 1, wherein the proximity sensor detects a touch of the person's hand to a knob of the pressure controller.

10. The method of claim 1, wherein the data is wirelessly transmitted by at least one of a radio signal and a light signal.

11. A pressure (vacuum) regulator system capable of reducing power consumption by waking a regulator upon detection of a person's hand proximity prior to adjustment of a pressure controller, comprising:
    means for defining a sampling time-window to sample a pressure in the pressure regulator system;
    means for generating a random number of pressure samples within the defined sampling time-window;
    means for acquiring data of the randomly generated number of pressure samples within the defined sampling time-window;
    means for detecting a proximity;
    means for adjusting the sampling time-window in response to a triggering of the means for detecting the proximity; and
    means for wirelessly transmitting the data to an output device.

12. The system of claim 11, wherein the means for wirelessly transmitting the data is selected from the group consisting of a computer, a smart phone, a tablet, and a netbook.

13. The system of claim 11, further comprising means for returning the adjusted sampling time-window to its initial defined value following a predetermined period of negligible change in the acquired data.

14. A reduced power consumption, non-mains pressure (vacuum) regulator system, comprising:
    a non-mains powered regulator controller capable of sampling pressure values in a sampling time window;
    an input port and an output port;
    an adjustment valve coupled to at least one of the input port and output port; a knob attached to the adjustment valve;
    an output pressure transducer coupled to the output port;
    a wireless transmitter connected to the output port; and
    a proximity detector coupled to the controller,
    wherein the proximity detector upon triggering adjusts a random pressure sampling time-window.

15. The system of claim 14, wherein the wireless transmitter connects to a mesh network.

16. The system of claim 14, wherein the wireless transmitter is configured to transmit at least one of a radio signal and a light signal.

17. The system of claim 14, wherein the output device is selected from the group consisting of a computer, a smart phone, a tablet, and a netbook.

18. The system of claim 14, wherein the proximity detector is a motion sensor.

19. The system of claim 14, wherein the proximity detector detects a touch of a person's hand to the knob.

20. A method of reducing power consumption in a pressure (vacuum) regulator system by waking the regulator upon detection of a person's hand proximity prior to adjustment of the pressure controller, comprising:
    initiating a sampling of pressure;
    acquiring a next sampling of pressure after a randomly generated time delay;
    adjusting the time delay in response to a triggering of a proximity sensor;

acquiring another sampling of pressure after adjustment of the adjusted time delay; and wirelessly transmitting the data to an output device.

21. The method of claim 20, further comprising the step of sending at least one of continuous and intermittent pressure information via email.

22. The method of claim 20, further comprising the step of wirelessly transmitting the data via a mesh network.

23. The method of claim 20, wherein the output device is selected from the group consisting of a computer, a smart phone, a tablet, and a netbook.

24. The method of claim 20, wherein the proximity sensor is a motion sensor.

25. The method of claim 20, wherein the proximity sensor detects a touch of the person's hand to a knob of the pressure controller.

26. The method of claim 20, wherein the data is transmitted by at least one of a radio signal and a light signal.

27. A pressure (vacuum) regulator system capable of reducing power consumption by waking the regulator upon detection of a person's hand proximity prior to adjustment of the pressure controller, comprising:

means for initiating a sampling of pressure; means for acquiring a sampling of pressure after a randomly generated time delay;

means for adjusting the time delay in response to triggering of a proximity sensor, wherein the means for acquiring acquires another sampling of pressure after adjustment of the adjusted time delay; and means for wirelessly transmitting the data to an output device.

* * * * *